(12) United States Patent
Barr et al.

(10) Patent No.: US 9,034,038 B2
(45) Date of Patent: May 19, 2015

(54) MOTION LIMITING INSERT FOR AN ARTIFICIAL INTERVERTEBRAL DISC

(75) Inventors: Bryan Barr, San Jose, CA (US); David Hovda, Mountain View, CA (US); Yves Arramon, Sunnyvale, CA (US)

(73) Assignee: SPINALMOTION, INC., Mountain View, CA (US)

( * ) Notice: Subject to any disclaimer, the term of this patent is extended or adjusted under 35 U.S.C. 154(b) by 1162 days.

(21) Appl. No.: 12/419,532

(22) Filed: Apr. 7, 2009

(65) Prior Publication Data

US 2010/0087868 A1 Apr. 8, 2010

Related U.S. Application Data

(60) Provisional application No. 61/044,290, filed on Apr. 11, 2008.

(51) Int. Cl.
*A61F 2/44* (2006.01)
*A61F 2/30* (2006.01)

(52) U.S. Cl.
CPC ........... *A61F 2/4425* (2013.01); *A61F 2/30734* (2013.01); *A61F 2002/30362* (2013.01); *A61F 2002/30515* (2013.01); *A61F 2002/30528* (2013.01); *A61F 2002/30604* (2013.01); *A61F 2002/30662* (2013.01); *A61F 2002/30663* (2013.01); *A61F 2002/3069* (2013.01); *A61F 2002/30884* (2013.01); *A61F 2002/30899* (2013.01); *A61F 2002/30904* (2013.01); *A61F 2002/443* (2013.01); *A61F 2220/0025* (2013.01); *A61F 2220/0033* (2013.01)

(58) Field of Classification Search
USPC ..................................................... 623/17.15
See application file for complete search history.

(56) References Cited

U.S. PATENT DOCUMENTS

| 3,486,505 A | 12/1969 | Morrison |
| 3,867,728 A | 2/1975 | Stubstad et al. |
| 4,309,777 A | 1/1982 | Patil |
| 4,531,917 A | 7/1985 | Linkow et al. |

(Continued)

FOREIGN PATENT DOCUMENTS

| DE | 3023353 A1 | 9/1981 |
| DE | 10035182 A1 | 2/2002 |

(Continued)

OTHER PUBLICATIONS

International Search Report and Written Opinion of PCT Application No. PCT/US09/40246, dated Aug. 27, 2009.

(Continued)

*Primary Examiner* — Thomas J Sweet
*Assistant Examiner* — Megan Wolf
(74) *Attorney, Agent, or Firm* — Wilson Sonsini Goodrich & Rosati

(57) ABSTRACT

A spacer for an artificial spinal disc arrangement is provided. The artificial disc arrangement includes an upper plate, a lower plate, and articulating surfaces between the upper and lower plates arranged to permit motion between the upper and lower plates. The spacer has a first surface for contacting the upper plate and a second surface for contacting the lower plate and is of sufficient thickness such that, when disposed between the upper and lower plates, the spacer limits motion between the upper and lower plates. An artificial disc, a method of limiting motion of an artificial disc in a patient, and a method of performing spinal disc surgery are also disclosed.

2 Claims, 3 Drawing Sheets

(56) References Cited

U.S. PATENT DOCUMENTS

| | | |
|---|---|---|
| 4,566,466 A | 1/1986 | Ripple et al. |
| 4,619,660 A | 10/1986 | Christiansen et al. |
| 4,673,407 A | 6/1987 | Martin |
| 4,759,766 A | 7/1988 | Buettner-Janz et al. |
| 4,759,769 A | 7/1988 | Hedman et al. |
| 4,834,757 A | 5/1989 | Brantigan |
| 4,863,477 A | 9/1989 | Monson |
| 4,904,261 A | 2/1990 | Dove et al. |
| 4,917,704 A | 4/1990 | Frey et al. |
| 4,932,969 A | 6/1990 | Frey et al. |
| 4,946,378 A | 8/1990 | Hirayama et al. |
| 4,997,432 A | 3/1991 | Keller |
| 5,035,716 A | 7/1991 | Downey |
| 5,057,108 A | 10/1991 | Shetty et al. |
| 5,071,437 A | 12/1991 | Steffee |
| 5,122,130 A | 6/1992 | Keller |
| 5,195,526 A | 3/1993 | Michelson |
| 5,258,031 A | 11/1993 | Salib et al. |
| 5,282,861 A | 2/1994 | Kaplan |
| 5,314,477 A | 5/1994 | Marnay |
| 5,320,644 A | 6/1994 | Baumgartner |
| 5,370,697 A | 12/1994 | Baumgartner |
| 5,394,457 A | 2/1995 | Leibinger et al. |
| 5,401,269 A | 3/1995 | Buttner-Janz et al. |
| 5,415,704 A | 5/1995 | Davidson |
| 5,458,642 A | 10/1995 | Beer et al. |
| 5,462,575 A | 10/1995 | Del Corso |
| 5,484,437 A | 1/1996 | Michelson |
| 5,489,307 A | 2/1996 | Kuslich et al. |
| 5,505,732 A | 4/1996 | Michelson |
| 5,507,816 A | 4/1996 | Bullivant |
| 5,534,030 A | 7/1996 | Navarro et al. |
| 5,556,431 A | 9/1996 | Buttner-Janz |
| 5,674,296 A | 10/1997 | Bryan et al. |
| 5,676,701 A | 10/1997 | Yuan et al. |
| 5,676,702 A | 10/1997 | Ratron |
| 5,683,465 A | 11/1997 | Shinn et al. |
| 5,702,450 A | 12/1997 | Bisserie |
| 5,709,683 A | 1/1998 | Bagby |
| 5,728,159 A | 3/1998 | Stroever et al. |
| 5,741,253 A | 4/1998 | Michelson |
| 5,776,198 A | 7/1998 | Rabbe et al. |
| 5,782,832 A | 7/1998 | Larsen et al. |
| 5,797,909 A | 8/1998 | Michelson |
| 5,824,094 A | 10/1998 | Serhan et al. |
| 5,836,948 A | 11/1998 | Zucherman et al. |
| 5,865,846 A | 2/1999 | Bryan et al. |
| 5,865,848 A | 2/1999 | Baker |
| 5,888,226 A | 3/1999 | Rogozinski |
| 5,895,428 A | 4/1999 | Berry |
| 5,899,901 A | 5/1999 | Middleton |
| 5,899,911 A | 5/1999 | Carter |
| 5,928,284 A | 7/1999 | Mehdizadeh |
| 5,989,251 A | 11/1999 | Nichols |
| 5,989,291 A | 11/1999 | Ralph et al. |
| 6,001,130 A | 12/1999 | Bryan et al. |
| 6,019,792 A | 2/2000 | Cauthen |
| 6,022,376 A | 2/2000 | Assell et al. |
| 6,039,761 A | 3/2000 | Li et al. |
| 6,039,763 A | 3/2000 | Shelokov |
| 6,080,155 A | 6/2000 | Michelson |
| 6,083,228 A | 7/2000 | Michelson |
| 6,086,613 A | 7/2000 | Camino et al. |
| 6,096,038 A | 8/2000 | Michelson |
| 6,132,465 A | 10/2000 | Ray et al. |
| 6,136,031 A | 10/2000 | Middleton |
| 6,139,551 A | 10/2000 | Michelson et al. |
| 6,139,579 A | 10/2000 | Steffee et al. |
| 6,143,033 A | 11/2000 | Paul et al. |
| 6,146,421 A | 11/2000 | Gordon et al. |
| 6,156,067 A | 12/2000 | Bryan et al. |
| 6,159,214 A | 12/2000 | Michelson |
| 6,162,252 A | 12/2000 | Kuras et al. |
| 6,174,311 B1 | 1/2001 | Branch et al. |
| 6,176,881 B1 | 1/2001 | Schar et al. |
| 6,193,757 B1 | 2/2001 | Foley et al. |
| 6,224,595 B1 | 5/2001 | Michelson |
| 6,224,607 B1 | 5/2001 | Michelson |
| 6,231,609 B1 | 5/2001 | Mehdizadeh |
| 6,235,030 B1 | 5/2001 | Zucherman et al. |
| 6,261,296 B1 | 7/2001 | Aebi et al. |
| 6,264,695 B1 | 7/2001 | Stoy |
| 6,290,726 B1 | 9/2001 | Pope et al. |
| 6,296,664 B1 | 10/2001 | Middleton |
| 6,315,797 B1 | 11/2001 | Middleton |
| 6,322,567 B1 | 11/2001 | Mittelstadt et al. |
| 6,336,941 B1 | 1/2002 | Subba Rao et al. |
| 6,348,071 B1 | 2/2002 | Steffee et al. |
| 6,368,350 B1 | 4/2002 | Erickson et al. |
| 6,368,351 B1 | 4/2002 | Glenn et al. |
| 6,375,681 B1 | 4/2002 | Truscott |
| 6,375,682 B1 | 4/2002 | Fleischmann et al. |
| 6,395,032 B1 | 5/2002 | Gauchet |
| 6,402,785 B1 | 6/2002 | Zdeblick et al. |
| 6,409,766 B1 | 6/2002 | Brett |
| 6,413,278 B1 | 7/2002 | Marchosky |
| 6,416,551 B1 | 7/2002 | Keller |
| 6,436,098 B1 | 8/2002 | Michelson |
| 6,440,139 B2 | 8/2002 | Michelson |
| 6,447,544 B1 | 9/2002 | Michelson |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,967 B1 | 2/2003 | Cauthen |
| 6,520,996 B1 | 2/2003 | Manasas et al. |
| 6,527,804 B1 | 3/2003 | Gauchet et al. |
| 6,533,817 B1 | 3/2003 | Norton et al. |
| 6,537,279 B1 | 3/2003 | Michelson |
| 6,554,863 B2 | 4/2003 | Paul et al. |
| 6,562,047 B2 | 5/2003 | Ralph et al. |
| 6,562,074 B2 | 5/2003 | Gerbec et al. |
| 6,565,574 B2 | 5/2003 | Michelson |
| 6,582,466 B1 | 6/2003 | Gauchet |
| 6,582,468 B1 | 6/2003 | Gauchet |
| 6,592,624 B1 | 7/2003 | Fraser et al. |
| 6,599,294 B2 | 7/2003 | Fuss et al. |
| 6,607,558 B2 | 8/2003 | Kuras |
| 6,607,559 B2 | 8/2003 | Ralph et al. |
| 6,610,092 B2 | 8/2003 | Ralph et al. |
| 6,623,525 B2 | 9/2003 | Ralph et al. |
| 6,645,248 B2 | 11/2003 | Casutt |
| 6,648,895 B2 | 11/2003 | Burkus et al. |
| 6,652,533 B2 | 11/2003 | O'Neil |
| 6,660,038 B2 | 12/2003 | Boyer, II et al. |
| 6,666,866 B2 | 12/2003 | Mertz et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,689,132 B2 | 2/2004 | Biscup |
| 6,706,068 B2 | 3/2004 | Ferree |
| 6,709,439 B2 | 3/2004 | Rogers et al. |
| 6,712,819 B2 | 3/2004 | Zucherman et al. |
| 6,712,825 B2 | 3/2004 | Aebi et al. |
| 6,723,097 B2 | 4/2004 | Fraser et al. |
| 6,726,720 B2 | 4/2004 | Ross et al. |
| 6,726,721 B2 | 4/2004 | Stoy et al. |
| 6,733,532 B1 | 5/2004 | Gauchet et al. |
| 6,740,118 B2 | 5/2004 | Eisermann et al. |
| 6,740,119 B2 | 5/2004 | Ralph et al. |
| 6,755,841 B2 | 6/2004 | Fraser et al. |
| 6,764,512 B2 | 7/2004 | Keller |
| 6,764,515 B2 | 7/2004 | Ralph et al. |
| 6,770,095 B2 | 8/2004 | Grinberg et al. |
| 6,790,233 B2 | 9/2004 | Brodke et al. |
| 6,793,678 B2 | 9/2004 | Hawkins |
| 6,814,737 B2 | 11/2004 | Cauthen |
| 6,821,298 B1 | 11/2004 | Jackson |
| 6,827,740 B1 | 12/2004 | Michelson |
| 6,830,570 B1 | 12/2004 | Frey et al. |
| 6,846,328 B2 | 1/2005 | Cauthen |
| 6,863,673 B2 | 3/2005 | Gerbec et al. |
| 6,875,213 B2 | 4/2005 | Michelson |
| 6,896,680 B2 | 5/2005 | Michelson |

(56) References Cited

U.S. PATENT DOCUMENTS

| | | |
|---|---|---|
| 6,899,735 B2 | 5/2005 | Coates et al. |
| 6,936,071 B1 | 8/2005 | Marnay et al. |
| 6,936,132 B2 | 8/2005 | Topolnitsky |
| 6,963,071 B2 | 11/2005 | Bristol |
| 6,964,686 B2 | 11/2005 | Gordon |
| 6,966,929 B2 | 11/2005 | Mitchell |
| 6,989,011 B2 | 1/2006 | Paul et al. |
| 6,994,727 B2 | 2/2006 | Khandkar et al. |
| 7,011,684 B2 | 3/2006 | Eckman |
| 7,022,138 B2 | 4/2006 | Mashburn |
| 7,025,787 B2 | 4/2006 | Bryan et al. |
| 7,044,983 B1 | 5/2006 | Cheng |
| 7,056,344 B2 | 6/2006 | Huppert et al. |
| 7,060,073 B2 | 6/2006 | Frey et al. |
| 7,066,958 B2 | 6/2006 | Ferree |
| 7,081,120 B2 | 7/2006 | Li et al. |
| 7,083,651 B2 | 8/2006 | Diaz et al. |
| 7,087,055 B2 | 8/2006 | Lim et al. |
| 7,097,648 B1 | 8/2006 | Globerman et al. |
| 7,115,132 B2 | 10/2006 | Errico et al. |
| 7,118,580 B1 | 10/2006 | Beyersdorff et al. |
| 7,147,665 B1 | 12/2006 | Bryan et al. |
| 7,153,325 B2 | 12/2006 | Kim et al. |
| 7,179,294 B2 | 2/2007 | Eisermann et al. |
| 7,182,784 B2 | 2/2007 | Evans et al. |
| 7,198,644 B2 | 4/2007 | Schultz et al. |
| 7,207,991 B2 | 4/2007 | Michelson |
| 7,214,244 B2 | 5/2007 | Zubok et al. |
| 7,217,291 B2 | 5/2007 | Zucherman et al. |
| 7,235,103 B2 | 6/2007 | Rivin |
| 7,250,060 B2 | 7/2007 | Trieu |
| 7,255,714 B2 | 8/2007 | Malek |
| 7,261,739 B2 | 8/2007 | Ralph et al. |
| 7,267,688 B2 | 9/2007 | Ferree |
| 7,270,679 B2 | 9/2007 | Istephanous et al. |
| 7,270,682 B2 | 9/2007 | Frigg et al. |
| 7,303,583 B1 | 12/2007 | Schar et al. |
| 7,318,839 B2 | 1/2008 | Malberg et al. |
| 7,326,250 B2 | 2/2008 | Beaurain et al. |
| 7,331,995 B2 | 2/2008 | Eisermann et al. |
| 7,429,270 B2 | 9/2008 | Baumgartner et al. |
| 7,442,211 B2 | 10/2008 | de Villiers et al. |
| 7,452,380 B2 | 11/2008 | Zubok et al. |
| 7,491,241 B2 | 2/2009 | Errico et al. |
| 7,494,508 B2 | 2/2009 | Zeegers |
| 7,549,995 B2 | 6/2009 | Schultz et al. |
| 7,708,776 B1 | 5/2010 | Blain et al. |
| 2001/0016773 A1 | 8/2001 | Serhan et al. |
| 2001/0029377 A1 | 10/2001 | Aebi et al. |
| 2002/0022845 A1 | 2/2002 | Zdeblick et al. |
| 2002/0035400 A1 | 3/2002 | Bryan et al. |
| 2002/0045904 A1 | 4/2002 | Fuss et al. |
| 2002/0068936 A1 | 6/2002 | Burkus et al. |
| 2002/0091392 A1 | 7/2002 | Michelson |
| 2002/0116009 A1 | 8/2002 | Fraser et al. |
| 2002/0123753 A1 | 9/2002 | Michelson |
| 2002/0128715 A1 | 9/2002 | Bryan et al. |
| 2002/0165550 A1 | 11/2002 | Frey et al. |
| 2002/0177897 A1 | 11/2002 | Michelson |
| 2002/0198532 A1 | 12/2002 | Michelson |
| 2003/0009224 A1 | 1/2003 | Kuras |
| 2003/0023245 A1 | 1/2003 | Ralph et al. |
| 2003/0028249 A1 | 2/2003 | Baccelli et al. |
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree |
| 2003/0083747 A1 | 5/2003 | Winterbottom et al. |
| 2003/0100951 A1 | 5/2003 | Serhan et al. |
| 2003/0125739 A1 | 7/2003 | Bagga |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0236426 A1 | 11/2004 | Ralph et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | de Villiers et al. |
| 2005/0021146 A1 | 1/2005 | de Villiers et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0192586 A1 | 9/2005 | Zuckerman et al. |
| 2005/0192670 A1 | 9/2005 | Zubok et al. |
| 2005/0197706 A1 | 9/2005 | Hovorka et al. |
| 2005/0203626 A1 * | 9/2005 | Sears et al. ............ 623/17.11 |
| 2005/0216076 A1 | 9/2005 | Taylor |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0251262 A1 | 11/2005 | de Villiers et al. |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | de Villiers et al. |
| 2006/0029186 A1 | 2/2006 | de Villiers et al. |
| 2006/0030857 A1 | 2/2006 | de Villiers et al. |
| 2006/0030862 A1 | 2/2006 | de Villiers et al. |
| 2006/0036325 A1 * | 2/2006 | Paul et al. ............ 623/17.14 |
| 2006/0041313 A1 | 2/2006 | Allard et al. |
| 2006/0041314 A1 | 2/2006 | Millard |
| 2006/0052870 A1 | 3/2006 | Ferree |
| 2006/0069439 A1 | 3/2006 | Zucherman et al. |
| 2006/0116768 A1 | 6/2006 | Krueger et al. |
| 2006/0142858 A1 | 6/2006 | Colleran |
| 2006/0142862 A1 | 6/2006 | Diaz et al. |
| 2006/0155378 A1 | 7/2006 | Eckman |
| 2006/0167549 A1 | 7/2006 | Mathys et al. |

(56) References Cited

U.S. PATENT DOCUMENTS

| | | |
|---|---|---|
| 2006/0178744 A1 | 8/2006 | de Villiers et al. |
| 2006/0178746 A1 | 8/2006 | Bartish, Jr. et al. |
| 2006/0195097 A1 | 8/2006 | Evans et al. |
| 2006/0200239 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0293752 A1 | 12/2006 | Moumene et al. |
| 2006/0293754 A1 | 12/2006 | de Villiers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0061011 A1 | 3/2007 | de Villiers et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270970 A1 | 11/2007 | Trieu |
| 2007/0282449 A1 | 12/2007 | de Villiers et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | de Villiers et al. |
| 2008/0051901 A1 | 2/2008 | de Villiers et al. |
| 2008/0119934 A1* | 5/2008 | Eckhardt ............. 623/17.16 |
| 2008/0125864 A1 | 5/2008 | de Villiers et al. |
| 2008/0133011 A1 | 6/2008 | de Villiers et al. |
| 2008/0154301 A1 | 6/2008 | de Villiers et al. |
| 2008/0154382 A1 | 6/2008 | de Villiers et al. |
| 2008/0215155 A1 | 9/2008 | de Villiers et al. |
| 2008/0221696 A1 | 9/2008 | de Villiers et al. |
| 2008/0228274 A1 | 9/2008 | de Villiers et al. |
| 2008/0228277 A1 | 9/2008 | de Villiers et al. |
| 2008/0294259 A1 | 11/2008 | de Villiers et al. |
| 2009/0043391 A1 | 2/2009 | de Villiers et al. |
| 2009/0048674 A1 | 2/2009 | Zubok et al. |
| 2009/0048677 A1 | 2/2009 | McLeod et al. |
| 2009/0076614 A1 | 3/2009 | Arramon |
| 2009/0105833 A1 | 4/2009 | Hovda et al. |
| 2009/0105834 A1 | 4/2009 | Hovda et al. |
| 2009/0105835 A1 | 4/2009 | Hovda et al. |
| 2009/0205188 A1 | 8/2009 | de Villiers et al. |
| 2009/0210060 A1 | 8/2009 | de Villiers et al. |
| 2009/0222101 A1 | 9/2009 | de Villiers et al. |
| 2009/0276051 A1 | 11/2009 | Arramon et al. |
| 2010/0004746 A1 | 1/2010 | Arramon |
| 2010/0016972 A1 | 1/2010 | Jansen et al. |
| 2010/0016973 A1 | 1/2010 | de Villiers et al. |
| 2010/0049040 A1 | 2/2010 | de Villiers et al. |
| 2010/0069976 A1 | 3/2010 | de Villiers et al. |
| 2010/0076558 A1 | 3/2010 | de Villiers et al. |

FOREIGN PATENT DOCUMENTS

| | | |
|---|---|---|
| EP | 0 333 990 A2 | 9/1989 |
| EP | 0 560 140 A1 | 9/1993 |
| EP | 0 560 141 A1 | 9/1993 |
| EP | 0 591 712 A1 | 4/1994 |
| EP | 0 820 740 | 1/1998 |
| EP | 1 142 544 A1 | 10/2001 |
| EP | 1 153 582 A2 | 11/2001 |
| EP | 1 250 898 A1 | 10/2002 |
| EP | 1 306 064 A1 | 5/2003 |
| EP | 1 344 493 A1 | 9/2003 |
| EP | 1 344 506 A1 | 9/2003 |
| EP | 1 344 507 A2 | 9/2003 |
| EP | 1 344 508 A3 | 9/2003 |
| EP | 1 405 615 | 4/2004 |
| EP | 1 417 940 A1 | 5/2004 |
| EP | 1 570 813 | 9/2005 |
| FR | 2 803 741 | 7/2001 |
| JP | 61-122859 | 6/1986 |
| JP | 63-164948 | 7/1988 |
| JP | 01-136655 | 5/1989 |
| JP | 06-007391 | 1/1994 |
| JP | 2002-521090 T | 7/2002 |
| JP | 2003-508119 T | 3/2003 |
| WO | WO 99/20209 | 4/1999 |
| WO | WO 99/30651 | 6/1999 |
| WO | WO 00/04851 | 2/2000 |
| WO | WO 00/35384 | 6/2000 |
| WO | WO 00/42954 | 7/2000 |
| WO | WO 01/01893 A1 | 1/2001 |
| WO | WO 01/15637 | 3/2001 |
| WO | WO 01/68003 A1 | 9/2001 |
| WO | WO 02/11650 | 2/2002 |
| WO | WO 2004/000170 | 12/2003 |
| WO | WO 2004/000171 | 12/2003 |
| WO | WO 2004/026187 A1 | 4/2004 |
| WO | WO 2004/041131 | 5/2004 |
| WO | WO 2004/054477 | 7/2004 |
| WO | WO 2005/004756 A2 | 1/2005 |
| WO | WO 2005/004756 A3 | 1/2005 |
| WO | WO 2005/004757 A1 | 1/2005 |
| WO | WO 2005/053580 A1 | 6/2005 |
| WO | WO 2005/072662 | 8/2005 |
| WO | WO 2005/112834 | 12/2005 |
| WO | WO 2006/119092 A2 | 11/2006 |
| WO | WO 2006/119092 A3 | 11/2006 |
| WO | WO 2007/121320 | 10/2007 |
| ZA | 03/9312 | 11/2003 |

OTHER PUBLICATIONS

Buttner-Janz, "The Development of the Artificial Disc," Introduction, pp. 1-18, Library of Congress Catalogue No. 92-75582, ISBN 0-9635430-0-8 (1989).

Hellier et al., "Wear Studies for Development of an Intervertebral Disc Prosthesis," *Spine*, vol. 17 No. 6 Supplement pp. 86-96 (1992).

Lee et al., "Impact Response of the Intervertebral Disc in a Finite-Element Model," *Spine* vol. 25, No. 19, pp. 2431-2439 (2000).

Lehuec et al., "Shock Absorption in Lumber Disc Prosthesis," *Journal of Spinal Disorders & Techniques*, vol. 16, No. 4, pp. 346-351(2003).

* cited by examiner

MOTION LIMITING INSERT FOR AN ARTIFICIAL INTERVERTEBRAL DISC

CROSS-REFERENCES TO RELATED APPLICATIONS

The present application claims the benefit under 35 USC 119(e) of U.S. Provisional Application No. 61/044,290 filed Apr. 11, 2008; the full disclosure of which is incorporated herein by reference in its entirety.

BACKGROUND OF THE INVENTION

The present invention relates to medical devices and methods. More specifically, the invention relates to intervertebral discs and devices and methods for limiting the motion of artificial intervertebral discs.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without interbody fusion of the two vertebrae adjacent to the disc. When the disc is partially or completely removed, it is necessary to replace the excised material to prevent direct contact between hard bony surfaces of adjacent vertebrae. Oftentimes, pins, rods, screws, cages and/or the like are inserted between the vertebrae to act as support structures to hold the vertebrae and graft material in place while they permanently fuse together. One typical fusion procedure is achieved by inserting a "cage" that maintains the space usually occupied by the disc to prevent the vertebrae from collapsing and impinging the nerve roots. The cage is used in combination with bone graft material (either autograft or allograft) such that the two vertebrae and the graft material will grow together over time, forming bridging bone between the two vertebrae. The fusion process typically takes 6-12 months after surgery. During this time external bracing (orthotics) may be required. External factors such as smoking, osteoporosis, certain medications, and heavy activity can prolong or even prevent the fusion process. If fusion does not occur, patients may require reoperation. It would be desirable to achieve immobilization of the vertebrae and maintain spacing between the adjacent vertebrae without the associated patient discomfort and long recovery time of traditional interbody fusion.

In an attempt to treat disc related pain without fusion provided by bridging bone, an alternative approach has been developed, in which a movable, implantable, artificial intervertebral disc (or "disc prosthesis") is inserted between two vertebrae. A number of different artificial intervertebral discs are currently being developed. For example, U.S. Patent Application Publication Nos. 2005/0021146, 2005/0021145, and 2006/0025862, which are hereby incorporated by reference in their entirety, describe artificial intervertebral discs. Other examples of intervertebral disc prostheses are the LINK SB CHARITÉ™ disc prosthesis (provided by DePuy Spine, Inc.) MOBIDISK™ disc prosthesis (provided by LDR Medical), the BRYAN™ cervical disc prosthesis (provided by Medtronic Sofamor Danek, Inc.), the PRODISC™ disc prosthesis or PRODISC-C™ disc prosthesis (from Synthes, Inc.), the PCM™ disc prosthesis (provided by Cervitech, Inc.), and the Maverick® disc (provided by Medtronic Sofamor Danek).

Although artificial discs provide a tremendous advantage over fusion in allowing the vertebrae to articulate after removal of the natural disc, sometimes an artificial disc does not provided the desired pain relief. In many cases where pain relief is not achieved, the artificial disc is removed and the patient then gets a traditional fusion. Removal of the disc is a difficult process generally involving anterior access to the spinal column through the abdominal cavity and removal of the disc often with additional bone. This procedure is complicated by the scar tissue which is present from the original surgery.

Accordingly, it would be desirable to have a device capable of limiting the motion of an artificial disc in a subsequent operation without needing to remove the entire disc. It would also be advantageous to provide a device capable of limiting motion of the disc which is inserted posteriorly.

In addition, although the existing artificial discs provide advantages over traditional fusion methods, many patients are not candidates for an artificial disc due to facet degeneration, instability, poor bone strength, previous surgery, multi-level disease, and pain sources that are non-discogenic. However, if there was a relatively easy way to convert an artificial disc to a fusion post operatively surgeons might be more willing to try the new artificial discs in patients which are on the borderline between being candidates for an artificial disc and a fusion.

Therefore, a need exists for an improved artificial disc or an insert for an artificial disc which can relatively easily convert an artificial disc to a more rigid fusion like device by the post operative addition of an insert.

BRIEF SUMMARY OF THE INVENTION

Embodiments of the present invention provide an artificial intervertebral disc and associated insert for limiting motion of the artificial disc as well as methods for limiting motion of an artificial disc.

In accordance with an aspect of the invention, a method is provided for limiting motion of a previously implanted articulating artificial intervertebral disc in a patient. The artificial disc comprises an upper plate, a lower plate, and articulating surfaces between the upper and lower plates arranged to permit motion between the upper and lower plates. The method comprises surgically accessing the previously implanted articulating artificial intervertebral disc and positioning a spacer arrangement between the upper and lower plates such that articulating motion between the upper and lower plates is at least substantially prevented.

In accordance with another aspect of the invention, a method is provided for performing spinal disc surgery on a patient. The method comprises performing a first operation to insert an artificial disc between an upper and a lower vertebrae of the patient. The artificial disc comprises an upper plate, a lower plate, articulating surfaces between the upper and lower plates to permit articulating motion between the upper and lower plates, and first means adapted to cooperate with second means for limiting articulating motion between the upper and lower plates. The second means is not inserted during the first operation.

In accordance with another aspect of the invention, an artificial spinal disc arrangement is provided including an artificial spinal disc comprising, a motion limiting insert and a locking mechanism. The artificial spinal disc includes an upper plate having an outer vertebral contacting surface and an inner surface and a lower plate having an outer vertebral contacting surface and an inner surface, wherein the inner surfaces of the upper and lower plates having cooperating surfaces configured to allow articulation of the upper and lower plates with respect to one another. The motion limiting insert is sized to fit between the upper and lower plates and configured to limit motion between the upper and lower plates to 10 degrees or less in any direction, wherein the motion limiting insert contacts the upper and lower plates and substantially surrounds an articulating surface of the artificial spinal disc. The locking mechanism is provided for locking the motion limiting insert to itself or to the upper or lower plates to hold the motion limiting insert in place on the artificial spinal disc.

In accordance with another aspect of the present invention, a spacer is provided for an artificial spinal disc arrangement. The artificial disc arrangement comprises an upper plate, a lower plate, and a core disposed between the upper and lower plates and having upper and lower surfaces for cooperating with the upper and lower plates to permit motion of the upper and lower plates on the core. The spacer has a first surface for contacting the upper plate and a second surface for contacting the lower plate and is of sufficient thickness such that, when disposed between the upper and lower plates, the spacer limits motion of the upper and lower plates on the core. The spacer is adapted to at least substantially encircle the core.

BRIEF DESCRIPTION OF THE DRAWINGS

The features and advantages of the present invention are well understood by reading the following detailed description in conjunction with the drawings in which like numerals indicate similar elements and in which.

DETAILED DESCRIPTION OF THE INVENTION

Figure 1:
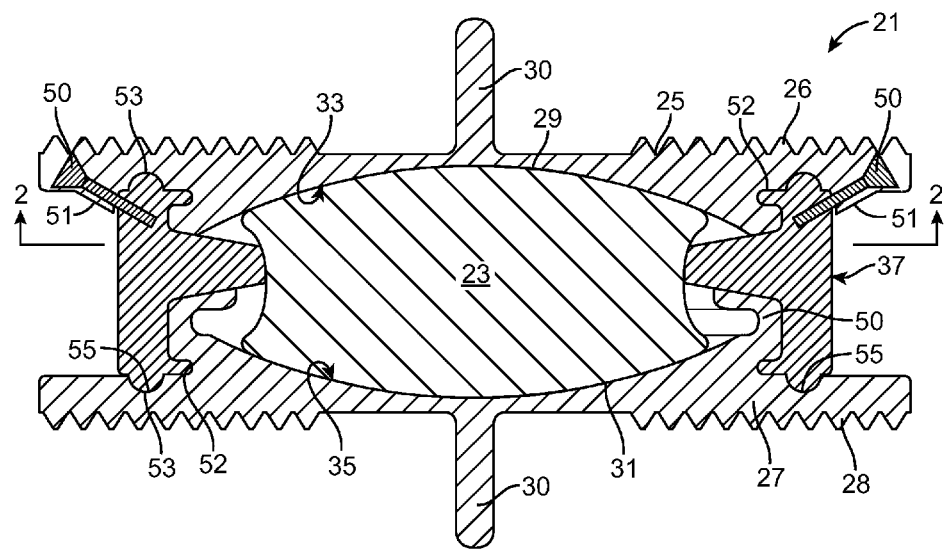
FIG. 1 is a cross-sectional view of a spinal disc arrangement viewed from a posterior side of the disc according to an aspect of the present invention.
Figure 2:
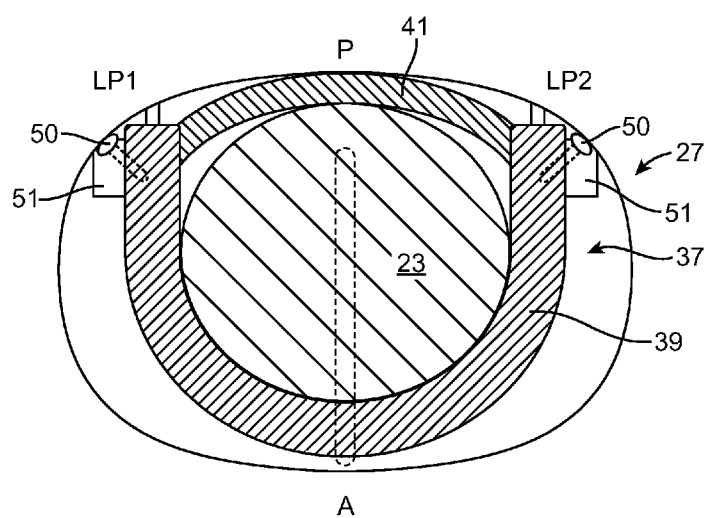
FIG. 2 is a cross-sectional view of the spinal disc arrangement taken at Section 2-2 of FIG. 1.

An artificial spinal disc 21 according to an aspect of the present invention for insertion in a patient is seen in FIGS. 1 and 2. The disc comprises a core 23 disposed between an upper plate 25 and a lower plate 27. The core 23 has upper and lower convex articulation surfaces 29 and 31. The upper and lower plates 25 and 27 have concave surfaces 33 and 35 corresponding to the convex surfaces 29 and 31 of the core 23 to permit relative motion of the upper and lower plates via sliding of the upper and lower plates on the core. A motion limiting insert or spacer 37 as will be described herein can be added to the artificial disc 21 after the artificial disc has been implanted in a patient. The motion limiting insert 37 is implanted in a surgery subsequent to the original disc replacement surgery in order to limit, restrict or eliminate motion between the upper and lower plates 25 and 27. The motion limiting insert 37 can be inserted in a minimally invasive procedure and can avoid the need for the highly invasive removal or revision surgery which is currently used if symptoms continue after artificial disc surgery.

The upper and lower plates 25 and 27 of the disc 21 as shown in FIGS. 1 and 2 each include serrated bone contacting surfaces 26 and 28 and one or more fin 30. Additional or alternative fixation members including teeth, bone integration coatings, prongs, and serrations can also be used. Although a disc design including a mobile core 23, two plates 25 and 27, and fins 30 has been illustrated, the motion limiting inserts 37 according to the present invention can also be used in other artificial disc designs including ball and socket designs and finless designs. In addition, although the articulation surfaces of the upper and lower plates 25 and 27 and the articulating surfaces of the core have been illustrated as spherical surfaces, other shaped articulating surfaces can also be used. For example, flat, cylindrical, kidney bean shaped, elliptical, or other shaped bearing surfaces may be used.

The disc 21 of FIGS. 1 and 2 also includes a retention ring 50 configured to cooperate with a rim 54 on the exterior of the core 23 to retain the core within the disc. However, other retention features may be used for retaining the core 23 in place of the retention ring 50. For example, retaining pins, slots, tabs, grooves, and flanges may also be used either alone or in combination.

The upper and lower plates 25 and 27 may also include annular grooves 52 configured to receive a grasping tool for holding the disc during an implantation procedure. Alternative features on the plates for engagement with an implantation instrument include grooves on the edges of the plates 25 and 27 or blind holes configured to receive prongs of an implantation instrument.

The disc 21 can be, but need not be, provided with a first structure as an original part of the disc which is adapted to cooperate with a second structure in the form of the motion limiting insert 37 added at a later date for limiting motion via sliding of the upper and lower plates 25 and 27 on the core 23. The first structure can form part of the disc 21 that is inserted between two vertebrae (not shown) during customary disc replacement surgery, without the second structure. In some aspects of the invention, the disc has no first structure, and the second structure is introduced to a conventional artificial disc and limits motion. Most commonly, the artificial disc 21 without the motion limiting insert 37 shown in FIG. 1 is inserted by accessing the vertebrae anteriorly through the patient. The second structure 37 can be inserted during a subsequent operation to limit motion via sliding of the upper and lower plates 25 and 27 on the core 23, such as when pain relief through disc replacement is not achieved.

In an aspect of the present invention, the second structure can be inserted posteriorly, substantially simplifying the procedure as compared to accessing the disc anteriorly. Alternatively, the artificial disc and/or the second structure (motion limiting insert) may be inserted by any of the known approaches including anterior, posterior, transverse, lateral extracavitary, trans-sacral and other approaches. When the approach for the insertion of the motion limiting insert is different from the original approach used to implant the disc, there is an advantage in avoiding the area of scar tissue from the first surgery. The posterior, transverse, or lateral approaches of inserting the motion limiting insert or spacer 37 may be performed minimally invasively by forming a series (two or three) keyhole openings at the site. As will be described in further detail below, two keyhole openings may be formed from the posterior at opposite sides of the previously implanted disc.

As seen in FIG. 1, the second structure comprises a spacer 37 which acts as a motion limiting insert. The first structure, if provided, can comprise a corresponding structure such as a groove, a detent, or some other structure on at least one of the upper and lower plates 25 and 27 adapted to cooperate with the spacer 37 to prevent movement of the spacer relative to the at least one of the upper and lower plates. In the embodiment of FIGS. 1 and 2, the first structure is a groove 55 extending along the anterior and lateral sides of each of the plates 25 and 27. The groove 55 is engaged by a corresponding rib 53 of the spacer 37. The cross sectional shape of the groove 55 and rib 53 is shown as concave/convex, but can be any other corresponding shape. The spacer 37 and one or both of the upper and lower plates 25 and 27 can alternatively comprise a cooperating detent and recess arrangement for attaching the spacer to at least one of the upper and lower plates.

The groove 55 and rib 53 arrangement can be used in conjunction with a fastener 50 for fixing the spacer 37 to one or both of the upper and lower plates 25 and 27. The fastener 50 can extend through a ridge 51 provided on one or both of the upper and lower plates 25 and 27 which may extend along at least the lateral sides of the plates. The grooves 55, fasteners 50, detents or other fasteners function to lock the spacer 37 in position with respect to the upper and lower plates 25 and 27 and can also prevent relative axial rotation between the first and second plates. When no fastening structures are provided between the spacer 37 and the upper and lower plates 25 and 27, the plates and the spacer 37 may continue to rotate with respect to one another allowing rotational motion in the disc space while the spacer substantially limits anterior-posterior or lateral bending motion.

The extent to which each type of motion is limited may vary depending on the particular patient's condition. For example, in many cases, the motion limiting insert is designed to substantially eliminate all motion including anterior/posterior articulation, lateral articulation, and axial rotation. In another case anterior/posterior articulation and lateral articulation is limited to a total of 10 degrees or less or in a patient require further restriction of motion to 2 degrees or less. In addition, the limitation on motion can be greater in one direction than in the other. The different limitation in motion for different directions is achieved either by contouring (varying the height) of the motion limiting insert 37 or by providing multiple motion limiting inserts on different sides of the disc.

The spacer 37 is shown with an inner surface having a shape which matches and cooperates with the shape of the inner surfaces of the plates 25 and 27 and comes into contact with outer surfaces of the core 23. The shape of the spacer 37 is designed to coordinate with a particular disc design and size to contact and maintain a constant space and/or angulation between the upper and lower plates 25 and 27. Contact and cooperation of the spacer inner surface with the core 23 outer surface is optional. For use with artificial discs having other core shapes or ball and socket type articulation surfaces, the spacer 37 may have a different inner surface profile than that shown in FIG. 1 to accommodate the shape of the core or other articulating surfaces. An interior shape of the semi-circular portion 39 can be shaped to match an exterior shape of the retention ring 50 and/or an exterior shape of the insertion instrument receiving grooves 52 on one or both of the upper and lower plates around all or part of the plates 25 and 27.

As seen in FIGS. 2-6, the spacer 37 can be adapted to at least substantially encircle the core 23 (or, if the core is removed, the position where the core would have been located). Because of the difficulty of gaining access to the anterior side of the disc 21, it can be useful for the spacer to be shaped to facilitate installation from a lateral posterior side of the disc to avoid interfering with the spinal column.

FIG. 2 shows an embodiment of a spacer 37 comprising a single semi-circular portion 39 that can be installed, for example, from one lateral posterior side LP1 of the disc 21, around the anterior side A, to the other lateral posterior side LP2 of the disc. A capping piece 41 extends from one lateral posterior side LP1 of the disc 21, around the posterior side P, to the other lateral posterior side LP2 of the disc. Extension of the capping piece 41 in the posterior direction will ordinarily be limited to avoid, inter alia, interference with the spinal column. The semi-circular portion 39 and capping piece 41 can be secured in place by means of screws 50 extending through one or both of the end plates 25 and 27. The capping piece 41 can also be secured to the semi-circular portion by any known connection method. The installation of the spacer 37 can be done via traditional surgical approaches or by minimally invasive keyhole surgery by forming small incisions at the two lateral posterior positions LP1 and LP2.

Figure 3:
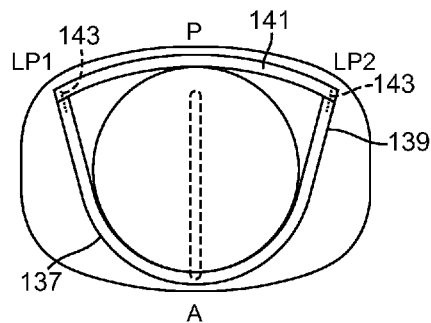
FIG. 3 is a schematic plan view of a portion of a spinal disc arrangement according to an aspect of the present invention.

FIG. 3 shows an embodiment of a spacer 137 comprising a single semi-circular portion 139 that can be installed, for example, from one lateral posterior side LP1 of the disc 21, around the anterior side A, to the other lateral posterior side LP2 of the disc. A capping piece 141 extends from one lateral posterior side LP1 of the disc 21, around the posterior side P, to the other lateral posterior side LP2 of the disc. The capping piece 141 may extend in an anterior direction into the space that would ordinarily be occupied by the core 23, such as by deforming the core or removing part of the core. The capping piece 141 can be fastened to the semi-circular portion 139, such as by fasteners 143 installed proximate the first and second lateral posterior sides of the disc. An interior shape of the semi-circular portion 139 can match an exterior shape of one or both of the upper and lower plates and the core.

Figure 4:
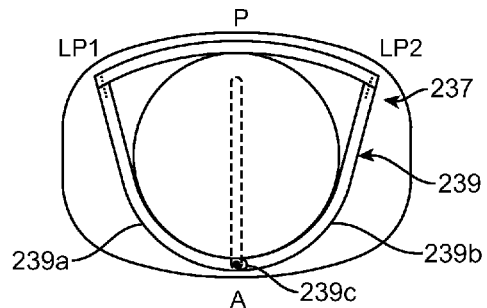
FIG. 4 is a schematic plan view of a portion of a spinal disc arrangement according to another aspect of the present invention.
Figure 5:
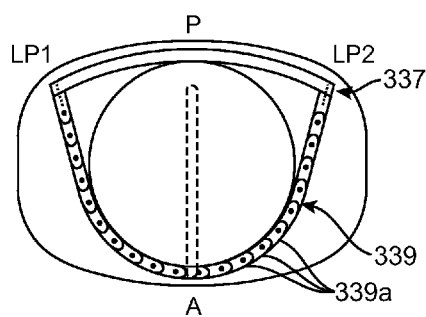
FIG. 5 is a schematic plan view of a portion of a spinal disc arrangement according to another aspect of the present invention.

To facilitate installation of the spacer, at least part of the spacer can be bendable around the anterior side A of the core 23. FIG. 4 shows a spacer 237 having a semi-circular piece 239 that comprises two curved or straight components 239a and 239b joined by a hinge 239c. FIG. 5 shows a spacer 337 having a semi-circular piece 339 that comprises a plurality of curved or straight components 339a that can be joined together in the manner of a chain. The spacers 137, 237, and 337 can be drawn around the core 23 by a cable (not shown) that may be easily inserted around the core due to its flexibility and can be inserted through a smaller more minimally invasive opening.

Figure 6:
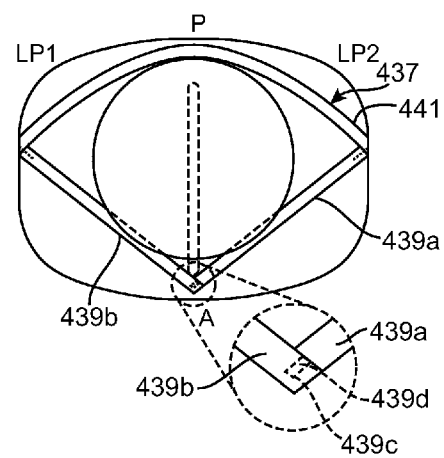
FIG. 6 is a schematic plan view of a portion of a spinal disc arrangement according to another aspect of the present invention.

FIG. 6 shows another embodiment wherein the spacer 437 substantially encircles the core 23. In the embodiment of FIG. 6, a first element 439a is installed from one lateral posterior side LP1 and a second element 439b is installed from the other lateral posterior side LP2 of the disc. An end of the first element 439a can have a first mating element 439c such as a protrusion proximate an anterior end of the first element that can mate with a second mating element 439d such as a protrusion receiving recess proximate an anterior end of the second element 439b when the ends of the first and second elements are brought together. Posterior ends of the first and second elements 439a and 439b can be joined to a capping piece 441.

While FIGS. 3-6 show embodiments wherein the spacer completely surrounds the core 23, it will be appreciated that the spacer might only partially surround the core, as well. For example, the capping pieces can be omitted entirely, or can be connected at only one side of the semi-circular or other pieces such that the spacer does not entirely surround the core. It will, of course, ordinarily be desirable that the spacer surround the core sufficiently such that substantial anterior/posterior and lateral movement of the upper and lower plates is prevented. For example, the spacers shown herein may surround the core on at least two opposite sides or surround at least 50% of the perimeter of the core.

Figure 7:
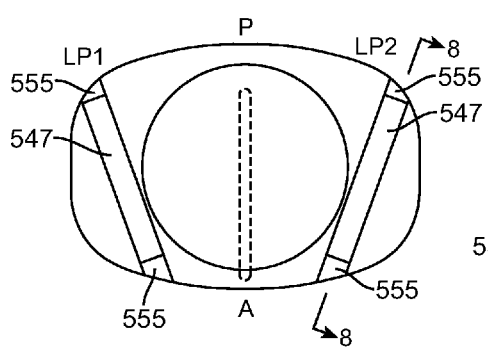
FIG. 7 is a schematic plan view of a portion of a spinal disc arrangement according to another aspect of the present invention.
Figure 8:
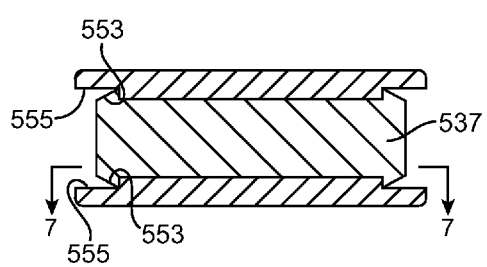
FIG. 8 is a partially cross-sectional view of a spinal disk arrangement of FIG. 7 taken at Section 8-8 of FIG. 7.

FIGS. 7 and 8 show an embodiment comprising at least two grooves 547 (not shown in FIG. 8) and the spacer comprises at least two spacers 537 (not shown in FIG. 7) adapted to be inserted in corresponding ones of the at least two grooves. As seen in FIG. 7, two of the grooves 547 can be angled relative to each other and define a largest gap between each other at opposite lateral posterior positions LP1 and LP2 of the artificial disc and a smallest gap between each other proximate an anterior portion A of the artificial disc. Alternately, the grooves 547 can be parallel to one another. The arrangement of the grooves facilitates installation of the two separate spacers 537 from the posterior of the patient at the lateral posterior positions LP1 and LP2. While not necessary, a capping piece, for example as described above, can be provided across a posterior side of the core. A detent 553 and recess 555 arrangement can be provided to better retain the spacers 537. In the embodiment of FIGS. 7 and 8, the detents 553 are formed as projections proximate ends of the spacers 537, and the recesses 555 are formed as notches at ends of the grooves 547.

Figure 9:
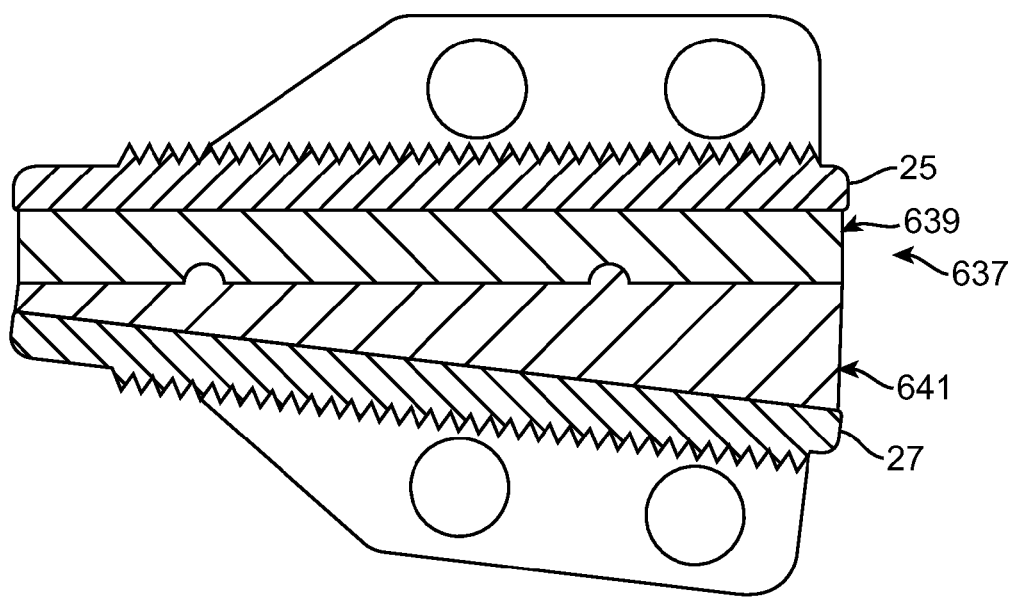
FIG. 9 is a schematic side view of a portion of a spinal disc arrangement according to an aspect of the present invention.

FIG. 9 shows an embodiment wherein the spacer arrangement 637 comprises upper and lower components 639 and 641. Locking structures such as detents and recesses, serrations, or fasteners can be provided on facing surfaces of the upper and lower components 639 and 641 for locking the components relative to each other and thereby preventing relative sliding of the components. The use of multiple components allows the height and lordosis to be tailored to the anatomy of the particular patient while providing fewer size parts. In the embodiment of FIG. 9 with multiple components, the upper and lower components may each include one or more parts to partly or fully surround the core, as shown in the embodiments of FIGS. 1-8.

In the embodiment of FIG. 9, at least one of the first and second components, i.e., the lower component 641, is wedge-shaped and is thicker toward an anterior end of the component than toward a posterior end of the component to accommodate lordosis. During insertion of the components, the wedge-shaped lower component 641 can be inserted first through the narrower, lateral posterior space between the upper and lower plates 25 and 27. The substantially flat upper component 639 can be installed afterward. This sequence can facilitate installation as it may be more difficult to fit the thick end of the wedge-shaped component 641 through the limited space available between the flat component 639 and the lower plate than to fit the thick end of the wedge-shaped component 641 through the space between the upper and lower plates and thereafter fit the flat component between the wedge-shaped component and the upper plate.

In another embodiment of the present invention, the core can include a channel or passageway there through and the motion limiting insert can include one or more parts which extend through the core to lock the core in place with respect to the insert and to the plates.

In a method according to an aspect of the present invention, a spacer arrangement 37 is positioned between the upper and lower plates 25 and 27 of a previously implanted articulating artificial intervertebral disc such that spinal motion via sliding of the upper and lower plates 25 and 27 on the core 23 is at least minimized, and can be substantially prevented. The spacer 37 can ordinarily be positioned between the upper and lower plates 25 and 27 via a posterior side of the patient.

In embodiments such as those shown in FIGS. 3-6, the core 23 is at least substantially encircled with the spacer arrangement 37. This can be accomplished by bending part of the spacer arrangement around an anterior side A of the core 23, such as where the spacer arrangement comprises a hinged spacer 237 or chain-like spacer 337 with portions that pivot relative to each other as seen in FIGS. 4 and 5. This can also be accomplished by fixing components of the spacer arrangement 437 to each other when proximate an anterior side of the core, such as with interengaging or fastening members at anterior ends of components of the spacer arrangement. Components of the spacer arrangement 137, 237, 337, and 447 can be fixed to each other proximate a lateral posterior side LP1 and/or LP2 of the core 23, such as by providing a substantially straight capping piece extending across or through the posterior side of the core 23 from one lateral posterior side to the other.

Positioning the spacer arrangement can comprise causing a spacer to cooperate with a corresponding structure such as a groove 47, or a fastener 49, or a detent 53 or a recess 55 on at least one of the upper and lower plates to prevent movement of the spacer relative to the at least one of the upper and lower plates. In this case, positioning the spacer arrangement can comprise, e.g., inserting the spacer 37 in a groove 47 in one or both of the upper and lower plates 25 and 27. It can also or alternatively comprise fixing the spacer 37 to at least one of the upper and lower plates 25 and/or 27, such as via a fastener 49 that may extend through, for example, a ridge 51 on the at least one of the upper and lower plates into the spacer 37. It can also or alternatively comprise attaching the spacer 37 to at least one of the upper and lower plates via cooperating detent 53 and recess 55 arrangement.

As seen with reference to FIGS. 7 and 8, at least two grooves 547 can be provided for receiving at least two spacers 537, and the method can comprise inserting the at least two spacers in corresponding ones of the at least two grooves. The at least two grooves 547 can be angled relative to each other and define a largest gap between each other at opposite lateral posterior positions LP1 and LP2 of the artificial disc and a smallest gap between each other proximate an anterior portion A of the artificial disc.

As seen in FIG. 9, the spacer arrangement 637 can comprise upper and lower components 639 and 641. A first one of the upper and lower components 639 and 641 can be inserted between the upper and lower plates 23 and 25 first, and the second one of the upper and lower components can subsequently be inserted between the upper and lower plates in contact with the first component. The first and second components 639 and 641 can be locked relative to each other.

One or both of the first and second components can be wedge-shaped to accommodate lordosis. Ordinarily, one of the components, such as the lower component 641, will be thicker toward an anterior end A of the component than toward a posterior end P of the component. The wedge-shaped component 641 can be inserted between the upper and lower plates 25 and 27 before inserting a non-wedge-shaped component 639 between the upper and lower plates.

Although the motion limiting insert has been described in association with the artificial disc shown in FIG. 1, it should be understood that the same or similar designs can also be used with the other known artificial discs. For example, the motion limiting insert can be designed to cooperate with the discs described in U.S. Patent Application Publication Nos. 2005/0021146, 2005/0021145, and 2006/0025862, which were previously incorporated by reference in their entirety. In addition, to the use with mobile core artificial disc designs, the motion limiting inserts can be modified to work with ball and socket type artificial disc designs or other disc designs and disc designs having a variety of different shaped articulating surfaces.

The motion limiting inserts described and shown herein may fill the entire height between the upper and lower plates 25 and 27. When the motion limiting inserts fill the entire height between the upper and lower plates 25 and 27 and the motion limiting insert is locked in place to both the plates, substantially all motion is prevented. However, the motion limiting insert can also be designed to limit the motion between the plates to a predetermined amount of motion which may be different for different directions. For example, the motion limiting insert may prevent all transverse motion while allowing up to 10 degrees total of anterior-posterior motion.

In the present application, the use of terms such as "including" is open-ended and is intended to have the same meaning as terms such as "comprising" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A method for limiting motion of a previously implanted articulating artificial intervertebral disc in a patient, the artificial disc comprising an upper plate, a lower plate, and a mobile core between the upper and lower plates arranged to permit motion between the upper and lower plates, the method comprising:

surgically accessing the previously implanted articulating artificial intervertebral disc; and positioning a spacer arrangement between the upper and lower plates such that articulating motion between the upper and lower plates is at least substantially prevented, wherein positioning the spacer arrangement comprises causing a spacer to cooperate with a corresponding structure on at least one of the upper and lower plates to prevent movement of the spacer relative to the at least one of the upper and lower plates and wherein the spacer arrangement comprises upper and lower components, and inserting a first one of the upper and lower components between the upper and lower plates, subsequently inserting a second one of the upper and lower components between the upper and lower plates in contact with the first component and locking the first and second components relative to each other wherein articulating surfaces between the upper and lower plates include the mobile core, the core having upper and lower articulating surfaces and the upper and lower plates having corresponding articulating surfaces, and the step of positioning the spacer comprises positioning the spacer substantially around the core.

2. A method for limiting motion of a previously implanted articulating artificial intervertebral disc in a patient, the artificial disc comprising an upper plate, a lower plate, and a mobile core between the upper and lower plates arranged to permit motion between the upper and lower plates, the method comprising:

surgically accessing the previously implanted articulating artificial intervertebral disc; and positioning a spacer arrangement between the upper and lower plates such that articulating motion between the upper and lower plates is at least substantially prevented, wherein positioning the spacer arrangement comprises causing a spacer to cooperate with a corresponding structure on at least one of the upper and lower plates to prevent movement of the spacer relative to the at least one of the upper and lower plates and wherein the spacer arrangement comprises upper and lower components, and inserting a first one of the upper and lower components between the upper and lower plates, subsequently inserting a second one of the upper and lower components between the upper and lower plates in contact with the first component and locking the first and second components relative to each other wherein one of the first and second components is wedge-shaped and is thicker toward an anterior end of the component than toward a posterior end of the component, the method comprising inserting the wedge-shaped component between the upper and lower plates before inserting a non-wedge-shaped component between the upper and lower plates.

* * * * *